United States Patent
Dubus

[11] Patent Number: 6,054,326
[45] Date of Patent: Apr. 25, 2000

[54] FLUID TESTING AND ANALYSING DEVICE AND METHOD

[76] Inventor: Yves F. P. Dubus, 20 bis, rue des Pêcheries, F-33120 Arcachon, France

[21] Appl. No.: 08/945,765
[22] PCT Filed: May 23, 1996
[86] PCT No.: PCT/FR96/00770
§ 371 Date: Oct. 31, 1997
§ 102(e) Date: Oct. 31, 1997
[87] PCT Pub. No.: WO96/37304
PCT Pub. Date: Nov. 28, 1996

[30] Foreign Application Priority Data

May 23, 1995 [FR] France .................................. 95 06140

[51] Int. Cl.$^7$ .............................. B01L 9/06; G01N 33/80
[52] U.S. Cl. ......................... 436/180; 436/174; 422/100; 422/103; 422/104; 73/864.01
[58] Field of Search ..................................... 436/174, 180, 436/183; 422/100, 103, 104; 604/411, 412; 73/864.01

[56] References Cited

U.S. PATENT DOCUMENTS

| | | |
|---|---|---|
| 4,058,363 | 11/1977 | Silbert . |
| 4,155,711 | 5/1979 | Zelagin et al. .......................... 422/104 |
| 4,160,803 | 7/1979 | Potts ...................................... 422/101 |
| 4,976,925 | 12/1990 | Porcher et al. ......................... 422/100 |
| 4,980,297 | 12/1990 | Haynes et al. .......................... 436/178 |
| 5,140,993 | 8/1992 | Opekun et al. . |
| 5,286,453 | 2/1994 | Pope ....................................... 422/100 |
| 5,360,012 | 11/1994 | Ebara et al. ............................. 128/764 |
| 5,556,544 | 9/1996 | Didier ..................................... 210/436 |
| 5,558,838 | 9/1996 | Uffenheimer ........................... 422/100 |
| 5,714,125 | 2/1998 | Sagstter .................................. 422/102 |

FOREIGN PATENT DOCUMENTS

| | | |
|---|---|---|
| 8505039 | 11/1985 | WIPO . |
| 8603008 | 5/1986 | WIPO . |
| 8701461 | 3/1987 | WIPO . |
| 9208988 | 5/1992 | WIPO . |

*Primary Examiner*—Long V. Le
*Attorney, Agent, or Firm*—Oppedahl & Larson, LLP

[57] ABSTRACT

A fluid testing and analysing device and a method therefor are described. The device includes, from its base up and in its upstanding configuration, a tube-holder (A) for receiving at least one partially or totally transparent tube (1) so that one wall or part of a wall thereof is visible; one or more tubes (1) forming a closed testing and observation chamber, closure means (4) for each tube, with a needle (3) extending therethrough and a flange (5), surrounding the needle, of smaller diameter than the closure means; a substantially vertical raised portion forming peripheral and/or internal walls surrounding the needles (3) and advantageously higher than the distance by which the needles project above the closure means (4); and, optionally, perforatable sheathes (11) placed on the portion outside the closed chamber (1). The device is particularly useful for human and animal biology applications.

20 Claims, 2 Drawing Sheets

FLUID TESTING AND ANALYSING DEVICE AND METHOD

BACKGROUND OF THE INVENTION

The present invention relates to a device and a process for carrying out tests and/or analyses of fluids, notably with a view to determining blood groups or performing compatibility tests. In particular, it relates to a device and a process which make it possible to carry out safe tests and analyses of fluids under simple and safe conditions, which make these tests and analyses particularly attractive.

This device and process are particularly suitable for carrying out tests and analyses without any contamination by or of the environment.

The invention relates quite particularly, but not exclusively, to a device and a process for determining blood groups, notably in connection with a blood transfusion, by a visual test in the presence of a reagent.

Several types of devices are already known in the art for determining a patient's blood group or for carrying out blood compatibility tests.

Thus, EP-A-0,054,087 describes an apparatus for testing fluids deposited in layers on supports, capable of imparting a centrifugal force to said fluids, to which is applied an appropriate antibody, in order to reveal the antigen-antibody compatibility. This apparatus is complicated to manufacture and manipulate. It requires control by an outside energy source.

EP-A-0,104,881 describes a device for transfusion compatibility tests designed to be used at the bedside of a patient who is to receive a transfusion. This device can be fixed to the blood bag, and receives, by capillarity, a specified quantity of the patient's blood, which is then contacted with an antiserum. The porous plastic member in which this capillarity is exerted should be such that only non-agglutinated blood can continue to migrate by capillarity. Such a member, which consists of an absorbent porous material, is not protected before being introduced into the blood-group-revealing antiserum.

French Patent A-2,586,815 describes a device for the determination of a blood group, comprising, for visual examination of a mixture of blood sample and test serum, at least one closed chamber and means for introducing the blood specimen into said chamber. Means are provided to evacuate the air from the chamber through a permeable hydrophobic membrane, in order to permit the specimen to penetrate thereinto without being opposed by an excess pressure of air. The blood from the receiver is injected by a syringe.

Document WO-A-85/05039 describes a test-tube holder comprising a vacuum-creating system, wherein the tubes containing samples to be tested have a plug at their upper end and an elastic stopper at their base designed to be perforated by a hollow needle. A partial vacuum is then created in the tubes. The total content of each tube is thus extracted in one operation, without the possibility of partial or repeated extractions.

Document WO-A-92/08988 discloses a complex and automated apparatus for taking liquid test samples and simultaneously cleaning the sampling system of test samples. This system comprises a serum loading station, a detection station, an index table for regulating the advance of the tubes toward a collection station, a station for sampling aliquot parts and a wash station. Here again, the sampling is done by means of a needle whose point is introduced into the respective tube, and a vacuum is then applied to the needle, by which the liquid is completely extracted from the tube.

Document WO-A-87/01461 describes a device for determining a blood group, wherein means make it possible to insert a blood sample to be tested and/or the test serum in a closed chamber where the reaction of the test serum with the blood is observed. In practice, a moving member such as a hollow needle effects the transfer, to the chamber, of an amount of blood determined by the degree of partial vacuum or negative pressure previously created in said chamber. More preferably, the device comprises a housing made of two parts each displaceable relative to the other and each displaceable relative to the needle, which then has two points perforating, respectively and successively, the wall of the sample receptacle and that of the chamber.

None of the prior art testing devices fully satisfies all the conditions currently required for such devices, such as optimum conditions of reliability, manageability and safety, particularly in the area of blood group determination, notably during blood transfusions.

The problems most frequently encountered during control tests and analyses in all areas consist, in fact, of the risks of pollution of the substance to be analyzed and of the risks of staining or contamination of the operator. On the other hand, the impossibility of preserving the reactions in time prevents storage of previously obtained results.

More particularly in the medical domain, the possibility of viral contaminations could sometimes make it awkward, even dangerous for the manipulator to do a blood compatibility check just before a transfusion, a check consisting in verifying the correlation between the patient's blood (recipient) and that contained in the blood bag (donor) designed to be transfused into the patient. In practice, the currently available devices do not offer all the advantages that are expected in this regard. Nor do they provide total safety with regard to the assignment of the results and their follow-up.

Hence a need existed for a reliable, safe and easily manipulable device for performing control tests and analyses, a device which can be used in all areas and particularly in human and veterinary biology.

It has now been found, unexpectedly, that these advantages, as well as others which will become more obvious on reading the following description, are offered by a device and process according to the present invention.

SUMMARY OF THE INVENTION

The object of the present invention is to provide such a device and a process for putting it into practice, facilitating better meeting the legitimate requirements of users and enabling the latter to work more comfortably and with greater peace of mind in obtaining results that are not disturbed by external causes and are completely safe.

The object of the present invention is also to provide a device and a testing and analytical procedure which exempts the user from complex manipulations and thus extends the range of its use to all persons, even to those without specialized training, and in all areas.

Another object of the present invention is to provide such a device in which there is no need to create vacuum or negative pressure in the test chamber and observation chamber.

In effect, it has appeared that, unexpectedly, the device according to the invention provides a simplicity, safety and reliability of use which could not be obtained until now, and which are achieved even when using personnel without special training.

These and other objects are achieved by a device for carrying out tests on a fluid sample comprising:

(a) at least one reaction tube, said reaction tube having a wall that is at least partially transparent, said reaction tubes having an opening at a top end thereof;

(b) a tube holder having said at least one reaction tube disposed therein with a transparent portion of the wall thereof visible from outside of the holder;

(c) at least one closure disposed in the opening of said at least one reaction tube;

(d) at least one needle extending through the at least one closure and providing a connection for passage of fluid from outside the reaction reaction tube into an interior space within the at least one reaction tube; and (e) a substantially vertical raised portion forming walls surrounding the needle and defining a space surrounding the needle for receiving a sample container, wherein the closure interacts with a deformable portion of a perforable sample container received with the device with the needle perforating the perforable portion of the sample container to press against the deformable portion of the sample container causing fluid in the sample container to be driven through the needle into the interior space with the reaction tube.

DETAILED DESCRIPTION OF THE INVENTION

The primary object of the invention is a device for performing tests and/or analyses of fluids, comprising at least one closed chamber and at least one needle for perforating the fluid sample receptacles, and comprising, from its base up in an upright position:

a tube holder for receiving at least one partially or totally transparent tube, so that one wall or part of a wall thereof is visible;

at least one tube designed to form a closed chamber for a test and for observation thereof;

closure means for each tube, comprising, in their center, a needle extending therethrough and with its point facing upwards, and at the base thereof, on the upper surface of said closure means, a central raised part or flange surrounding the needle and having a smaller diameter than the diameter of said closure means; and a substantially vertical raised portion forming peripheral and/or internal walls surrounding the needles and advantageously higher than the distance by which the needles project above said closure means; and optionally, perforable sheaths placed on the part of the needles outside said closed chamber. This device is designed to be used in cooperation with sampling tubes of the fluid to be tested or of test fluid, comprising a perforable and deformable closure means, and/or flexible perforable hoses welded at their ends and containing a sample of fluid to be tested or test fluid.

For use of flexible hoses, the device is advantageously completed by a member forming a housing for their introduction over at least one needle to permit their non-throughgoing perforation by at least one of the above needles.

According to a preferred embodiment, the device according to the invention comprises a tube holder combined with at least one member forming a housing for combined use of test tubes and flexible test sample hoses.

The invention also relates to a process for carrying out tests and/or analyses of fluids, consisting in the use of a device as described above and below, and comprising the steps of:

perforation and deformation under pressure of the closure means of a tube or of a flexible hose containing a sample of fluid to be tested or of test fluid, for introduction of an appropriate amount of test sample in at least one closed chamber comprising a closure means provided with a perforating and introduction needle;

repetition of the above step until all the test reagents and/or all the samples to be tested or to be analyzed have been introduced in the respective closed chambers; and examination of the reaction chambers in question.

Below, the invention is described in more concrete terms by reference to the attached drawings, which in no way limit said invention, and in which:

For greater convenience, the invention will be described below by referring most frequently to such use. However, it should be understood that this particular application serves only to give a more precise illustration of the invention, and in no way limits the scope thereof.

Figure 1:
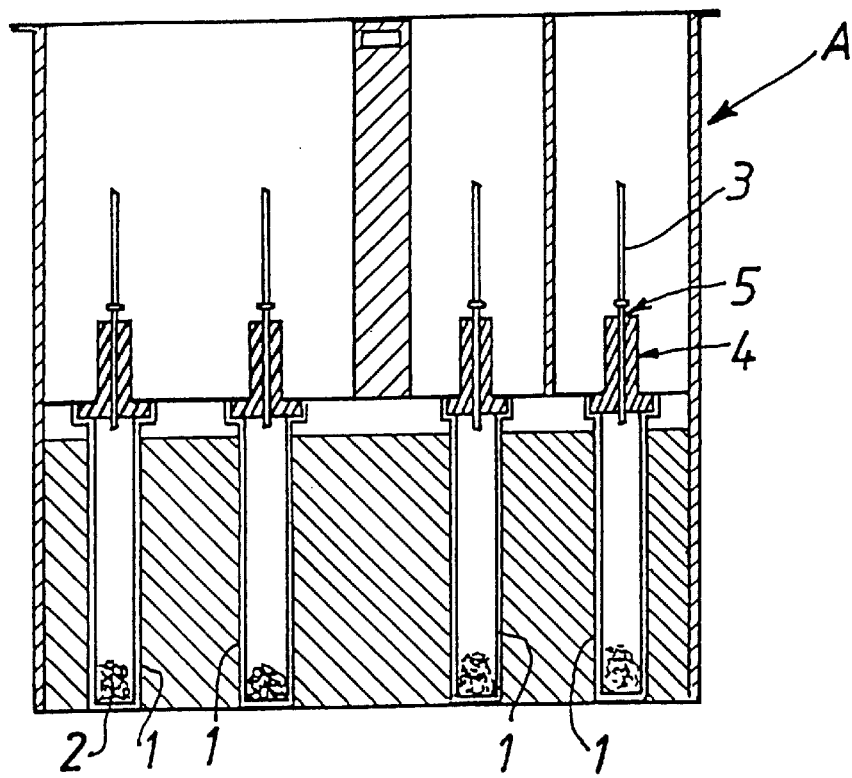
FIG. 1 represents, in schematic longitudinal section taken along a median vertical plane, an embodiment of the device of the invention in the upright position.
Figure 2:
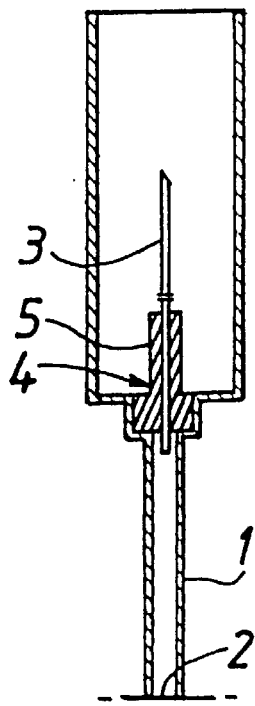
FIG. 2 is a schematic cross-sectional view of the device according to FIG. 1.

As shown in FIGS. 1 and 2, the device according to the invention comprises a tube holder A making it possible to maintain, in the upright position, at least one tube 1, which may or may not already contain a reagent 2 that is appropriate for the test to be carried out. The reagent may be introduced previously into the tube 1 before its obturation. This should be the case if said reagent is solid.

The tube holder A may be made of any material, preferably of plastic material, and it should leave visible at least portions of the wall of the tubes which it holds. In practice, this can be achieved either by choosing an intrinsically transparent material for said tube holder, or by having no wall in the tube holder opposite the portions of tube walls which must meet this condition. All or part of the tube holder and/or tubes may be, e.g., of glass or a plastic material such as polypropylene, polycarbonate, polyethylene, or others.

The tubes 1 may be introduced into appropriate receptacles of the tube holders or constitute an integral part thereof, advantageously in the form of cells arranged in the tube holder itself. They may have any given cross-section, e.g., square, triangular, circular, polygonal or other. An ovoid cross-section is preferred, so as not to create capillarity and electrostatic adhesion problems of the reagents and reaction products at the corners of a section having right angles or acute angles.

Tubes of small cross-section are preferred, where a small volume of reagent suffices. The height of the tube facilitates the "to-and-fro movement" of the reaction mixture when an alternating rocking movement is imparted to the device, and thus optimizes the "reading" of the reaction.

The upper orifice of the tube 1 is traversed in its center by a needle 3 which is made integral with a closure means 4 appropriate for plugging the orifice of said tube 1. This closure means may be of any material conventionally used for said function; it should be sufficiently rigid. According to a preferred embodiment, the needle/closure means assembly, as well as possibly the central raised part or flange 5 above it, may be obtained by molding techniques known to persons skilled in the art. In a variant, said flange may be detachable and be left to slide freely on the needle, or preferably it may be fixed in an adherent manner thereto or to the surface of the plug facing the point of the needle.

The raised portion may be realized by appropriate prolongation of the walls of the tube holder in the upright position, in direct prolongation thereof, or displaced relative to them. It is advantageously profiled in such a way, or has means on its walls facing the interior of the device that are so arranged, that a guidance is assured for the tubes 6 and/or housings 7 containing samples to be tested.

Figure 3:
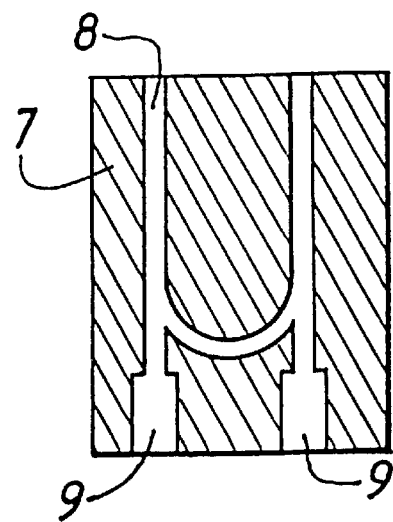
FIG. 3 is a partial sectional view of a housing for flexible tube.

As shown in FIG. 3, the housing 7 preferably consists of a block of dimensions suitable for its introduction, such as described above, and comprising, in the position of use, either a U-shaped channel 8 opening out to the top, or a substantially linear channel opening out laterally, as well as at least one nontraversing and substantially vertical bore 9, putting into communication said channel and the exterior on the lower surface of the housing.

According to an advantageous embodiment, the housing 7 comprises at least two bores and, optionally, it also has means for exerting pressures on the flexible hose 10, once the latter has been introduced into the housing, and means 12 for locking the housing into its position of use and preferably for preventing it from being removed after performance of the test, e.g., means in the form of reverse-lock pins in or near the guides used for its introduction into the tube holder.

To further improve the safety of the device with regard to the risk of staining or contamination, as well as to eliminate the risks of evaporation of the reagent before use, it is advantageous to provide the portions of the needles external to the test tubes with a perforable sheath 11 which is tight to liquids and preferably also to gases, e.g., one made of flexible plastic material such as polyvinyl chloride or rubber latex. This sheath, which in practice has the general form of a condom, is designed to be perforated by the needle, and is then folded into an accordion shape between the base of the needle and the plug of the sampling tube, where it contributes to improving the tightness, if necessary.

With regard more particularly to the domain of tests and analyses in human and veterinary biology, it has been found—as will be shown further on—that the device according to the invention is especially suitable for use in combination with all types of conventional sampling tubes with closure systems having the required perforability and flexibility characteristics.

To use the device according to the invention, a stoppered tube containing a sample is placed in an upside down position on the point of a needle of one of the tubes of the tube holder and a downward vertical pressure is applied thereto so as to deform the flexible stopper of this tube by said flange, in order to exert therein a fluid pressure sufficient to have one or more drops of the sample emerge from said tube. Said operation may be repeated as many times as necessary. Likewise, if the sample is contained in a flexible hose, the latter is introduced in a housing unit such as described above, which itself is brought opposite to at least one needle to permit a nontraversing perforation of the hose by said needle, and at least one pressure is exerted on the hose on at least one end thereof projecting from the housing, said pressure being applied either manually or by assisted pressure, or by means of a pressing member integral with the housing, or by downward vertical pressure on the housing itself, and doing so as many times as necessary. Here again, each pressure exerted on the hose has the effect of forcing at least one drop of sample fluid to pass through the channel of the needle into the corresponding tube, forming a closed reaction chamber.

The reaction showing the result of the test is of a known type. It is the result of a change in the mixture of the reagent contained or previously introduced into the reaction chamber and the sample to be analyzed, e.g., of blood whose blood group is being determined or checked in this manner. It makes use of either solid or liquid reagents, possibly on a support, reagents which are capable in the presence of a sample responding to the test of eliciting either a colored reaction or agglutination or other types of reactions observable by the human eye and/or by means of evaluation apparatus, such as, e.g., a clouding measurable by turbidimetry, or hemolysis. In practice, the device according to the invention is designed to be used for observing the test results directly by the naked eye.

According to the inventions identification of the samples tested is facilitated by the possibility offered by the tube holder of receiving clear or coded information on at least some of its visible surfaces, information suitable for perfect monitoring and increased safety of the tests. In addition, this device may, it desired, be connected to an automated recognition system, advantageously on the basis of numerical criteria.

According to a preferred variant for medical applications, particularly for blood transfusion, this device may be equipped with a chart or other support provided with a chip and capable of preliminary storage, by appropriate means, of the digital imprint and other data relating to the patient to be transfused and/or data concerning the bag of blood to be transfused.

The device according to the invention may be used for all types of tests, particularly but not exclusively in human or veterinary biology, especially for virological tests (e.g., HIV, among others) or bacteriological tests (e.g., in urinalyse. or cerebrospinal fluid puncture).

The tests carried out in this manner respond well to the requirements of instantaneousness and rapidity of results, while providing the manipulator user with a guarantee that there are no risks of contamination. Then, the reactions used may be hemagglutination reactions, latex agglutination reactions, or any other type of reaction that can be interpreted by the naked eye.

The simplicity of use of this device, which is ready for use, permits its use by all persons, even by those without any special knowledge of biology, and particularly by all hospital physicians, private physicians, nurses, patients themselves, or private persons.

Figure 4:
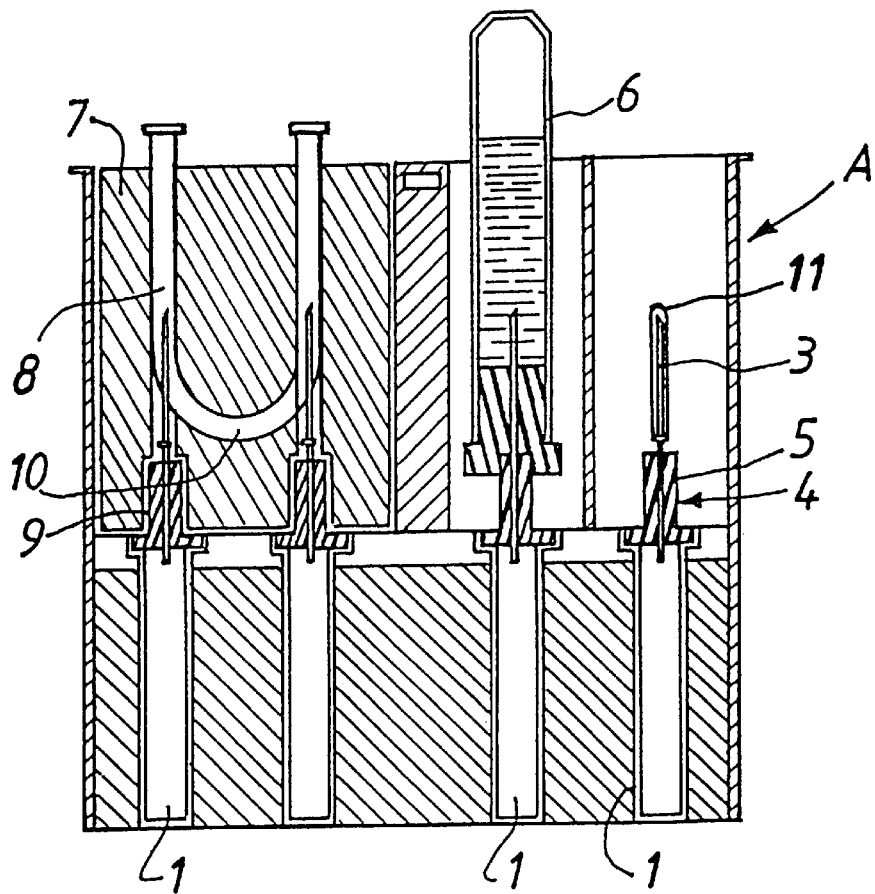
FIG. 4 is a schematic cross-sectional view taken along a median vertical plane of the device according to FIG. 1, in the upright position.

An illustrative example of an application in this area is given below, by reference to FIG. 4 of the appended drawings.

The device according to the invention in the variant of embodiment cited was used to carry out, immediately before a transfusion, a blood compatibility check, commonly called "final test at the patient's bedside." This test consisted in verifying the correlation between the patient's blood (recipient) and that contained in the bag of blood (donor) designed, in principle, to be transfused to the patient.

Figure 5:
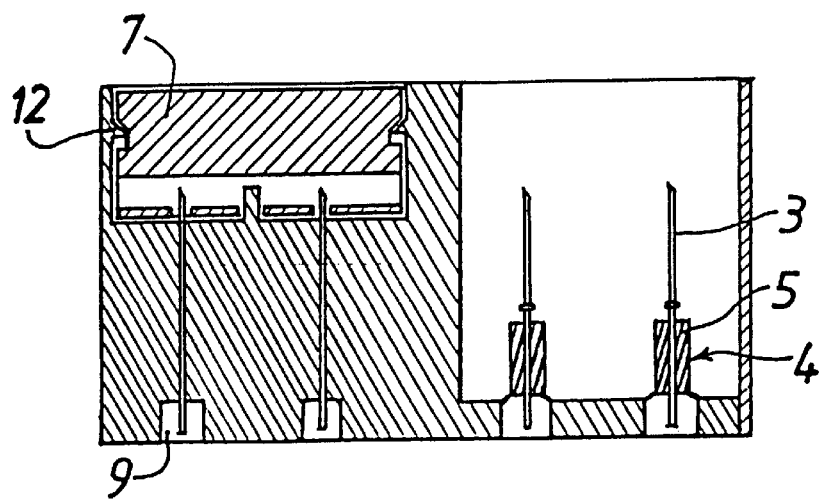
FIG. 5 is a partial schematic sectional view of a variant of housing, snapped onto a testing and/or analytical device according to FIG. 1, with only the upper part of said housing being shown.

A sample container with two contiguous chambers as shown in FIG. 5, capable of being simultaneously activated by perforation of a hose initially connected to the transfusion bag and introduced by means of an appropriate housing was used, respectively, for a reaction of the donor's blood with an anti-A test serum and a reaction with an anti-B test serum.

The two other chambers, each having a guide for the introduction of sample tubes, were used, respectively, for a reaction of the patient's blood with an anti-A test serum and a reaction with an anti-B test serum.

The samples originated, respectively:

from a blood sample tube of a type generally used in medicine, having a perforable and deformable closure means, from a tubing commonly called "hose or tube" integral with the transfusion bags and containing a small volume of blood.

They were contacted in the respective closed chambers with a test serum that was already present therein, namely with the anti-A test serum or the anti-B test serum, depending on the case, by perforation applying pressure on the needles carried by the respective reaction chambers as indicated above, so as to make at least one drop of blood fall each time into the reaction chamber.

For better performance of the agglutination reactions, the device was "moved to and fro" several times, to make it possible to spread the reaction product over nearly the entire surface of a wall of the tubes.

On "reading," the presence of agglutination indicates the presence, on the surface of the red blood cells tested, of the antigen corresponding to the antibody contained in the reaction chamber. By contrast, a homogeneous mixture without any trace of agglutination indicates the absence, on the surface of the red blood cells, of the antigen corresponding to the antibody contained in the reaction chamber.

The transfusion may be carried out if the results obtained in the two chambers reserved to the donor are equivalent to the results obtained in the two chambers reserved to the recipient.

For greater safety and for recording the results without any risk of confusion, all or part of the surface of the device opposite to that on which the reading of the results is made may bear one or more labels, comprising and/or receiving useful indications.

I claim:

1. A device for carrying out tests on a fluid sample comprising:
   (a) at least one reaction tube, said reaction tube having a wall that is at least partially transparent, said reaction tubes having an opening at a top end thereof;
   (b) a tube holder having said at least one reaction tube disposed therein with a transparent portion of the wall thereof visible from outside of the holder;
   (c) at least one closure disposed in the opening of said at least one reaction tube;
   (d) at least one needle extending through the at least one closure and providing a connection for passage of fluid from outside the reaction tube into an interior space within the at least one reaction tube; and
   (e) a substantially vertical raised portion forming walls surrounding the needle and defining a space surrounding the needle for receiving a sample container, wherein the closure interacts with a deformable portion of a perforable sample container received with the device with the needle perforating the perforable portion of the sample container to press against the deformable portion of the sample container causing fluid in the sample container to be driven through the needle into the interior space with the reaction tube.

2. The device according to claim 1, wherein the closure comprises a base portion having a diameter for insertion in the opening of the reaction tube, and a flange portion having a smaller diameter than the base portion, said flange portion surrounding a portion of the needle and extending from the base portion of the closure outwards from the opening of the reaction tube.

3. The device according to claim 1, further comprising at least one perforable sheath disposed over the at least one needle.

4. The device according to claim 1, further comprising at least one sample container disposed within the space defined by the vertical walls.

5. The device according to claim 4, wherein the sample container comprises a housing for receiving a perforable, flexible tube containing a fluid sample said housing comprising a body having a channel formed therein for receiving the perforable flexible tube and at least one bore extending from an exterior surface of the housing into said channel to provide access for perforation of flexible tube in the housing by the needle.

6. The device according to claim 5, wherein the channel in the body of the housing is U-shaped.

7. The device according to claim 6, wherein the closure comprises a base portion having a diameter for insertion in the opening of the reaction tube, and a flange portion having a smaller diameter than the base portion, said flange portion surrounding a portion of the needle and extending from the base portion of the closure outwards from the opening of the reaction tube.

8. The device according to claim 6, further comprising at least one perforable sheath disposed over the at least one needle.

9. The device according to claim 5, wherein the closure comprises a base portion having a diameter for insertion in the opening of the reaction tube, and a flange portion having a smaller diameter than the base portion, said flange portion surrounding a portion of the needle and extending from the base portion of the closure outwards from the opening of the reaction tube.

10. The device according to claim 5, further comprising at least one perforable sheath disposed over the at least one needle.

11. The device according to claim 5, wherein at least two bores are formed in the body of the housing, further comprising means for applying pressure on a perforable, flexible tube received within the channel.

12. The device according to claim 5, wherein the at least one reaction tube is formed as an integral part of the tube holder.

13. The device according to claim 5, further comprising a chip for storage of information concerning a patient or a sample.

14. A method for carrying out tests on a fluid sample comprising the steps of:
   (a) placing the fluid sample into a perforable and deformable sample container;
   (b) inserting the sample container into a device comprising
      at least one reaction tube, said reaction tube having a wall that is at least partially transparent, said reaction tubes having an opening at a top end thereof;

a tube holder having said a reaction tube disposed therein with a transparent portion of the wall thereof visible from outside of the holder;

a closure disposed in the opening of said at least one reaction tube;

a needle extending through the closure and providing a connection for passage of fluid from outside the reaction tube into an interior space within the reaction tube; and a substantially vertical raised portion forming walls surrounding the needle and defining a space surrounding the needle for receiving the sample container, (c) perforating the sample container with the needle and applying pressure to deform the sample container, thereby transferring at least a portion of the fluid sample from the sample container to the reaction tube for testing.

15. The method of claim 14, wherein the reaction tube contains a reagent for reaction with the sample fluid.

16. The method according to claim 14, wherein the closure comprises a base portion having a diameter for insertion in the opening of the reaction tube, and a flange portion having a smaller diameter than the base portion, said flange portion surrounding a portion of the needle and extending from the base portion of the closure outwards from the opening of the reaction tube.

17. The method according to claim 14, wherein the sample container comprises a housing for receiving a perforable, flexible tube containing a fluid sample said housing comprising a body having a channel formed therein for receiving the perforable flexible tube and at least one bore extending from an exterior surface of the housing into said channel to provide access for perforation of flexible tube in the housing by the needle.

18. The method according to claim 17, wherein the channel in the body of the housing is U-shaped.

19. The method according to claim 18, wherein the closure comprises a base portion having a diameter for insertion in the opening of the reaction tube, and a flange portion having a smaller diameter than the base portion, said flange portion surrounding a portion of the needle and extending from the base portion of the closure outwards from the opening of the reaction tube.

20. The method according to claim 17, wherein at least two bores are formed in the body of the housing, and the device further comprises means for applying pressure on a perforable, flexible tube received within the channel.

* * * * *